United States Patent [19]

von Bonin et al.

[11] 4,320,067
[45] Mar. 16, 1982

[54] PROCESS FOR THE PREPARATION OF MODIFIED POLYISOCYANATES

[75] Inventors: Wulf von Bonin; Helmut Kleimann, both of Leverkusen; Hans-Albrecht Freitag, Bergisch-Gladbach, all of Fed. Rep. of Germany

[73] Assignee: Bayer Aktiengesellschaft, Leverkusen, Fed. Rep. of Germany

[21] Appl. No.: 228,513

[22] Filed: Jan. 26, 1981

[30] Foreign Application Priority Data

Jan. 31, 1980 [DE] Fed. Rep. of Germany ....... 3003543

[51] Int. Cl.$^3$ ............... C07C 119/042; C07C 119/045; C07C 119/048
[52] U.S. Cl. ........................ 260/453 AR; 260/453 A; 260/453 AM; 260/453 AL; 544/400
[58] Field of Search .... 260/453 A, 453 AR, 453 AM, 260/453 AL

[56] References Cited

U.S. PATENT DOCUMENTS

| | | | |
|---|---|---|---|
| 3,903,126 | 9/1975 | Woerner et al. | 260/453 AB |
| 3,943,158 | 3/1976 | Dietrich et al. | 260/453 A |
| 4,118,411 | 10/1978 | Reiff et al. | 260/453 SP |
| 4,147,714 | 4/1979 | Hetzel et al. | 260/453 AB |
| 4,264,519 | 4/1981 | Hennig et al. | 260/453 AB |

FOREIGN PATENT DOCUMENTS 1263609  2/1972  United Kingdom .

*Primary Examiner*—Dolph H. Torrence
*Attorney, Agent, or Firm*—Gene Harsh; Joseph C. Gil; Lyndanne M. Whalen

[57] ABSTRACT

A process for preparing modified polyisocyanates in which an organic polyisocyanate is reacted with a polyamine present in less than stoichiometric amount. Polyamines suitable to this process include (a) polyamines having more than three nonaromatically bound, basic nitrogen atoms of which at least two are primary and/or secondary amino nitrogen atoms, and (b) polyamine mixtures having an average of more than three nonaromatically bound, basic nitrogen atoms of which at least two are primary and/or secondary amino nitrogen atoms. These modified polyisocyanates are particularly useful starting materials for production of polyurethane plastics by the isocyanate-polyaddition process.

5 Claims, No Drawings

PROCESS FOR THE PREPARATION OF MODIFIED POLYISOCYANATES

BACKGROUND OF THE INVENTION

This invention relates to a process for the preparation of modified polyisocyanates in which organic polyisocyanates are reacted with a specific type of organic polyamine.

The conversion of polyisocyanates to ureas or polyureas by reacting a polyisocyanate with primary or secondary amines is well known. This reaction is much more vigorous than a reaction of polyisocyanates in which primary or secondary alcohols are used rather than amines (particularly when the amine reaction is carried out without a diluent). The heat generated during the conversion frequently makes it difficult to control the temperature of the reaction (see, for example, British Pat. No. 1,263,609).

SUMMARY OF THE INVENTION

It is an object of the present invention to provide a process for the preparation of modified polyisocyanates which permits greater control of the temperature of reaction.

It is also an object of the present invention to provide a method for making modified polyisocyanates which are particularly useful in the preparation of polyurethane plastics according to the isocyanatepolyaddition process.

These and other objects which will be apparent to those skilled in the art are accomplished by reacting organic polyisocyanates with less than stoichiometric quantities of polyamines, which polyamines are either (a) polyamines containing more than three nonaromatically bound, basic nitrogen atoms, of which at least two are primary and/or secondary amino nitrogen atoms, or (b) a polyamine mixture which contains more than three nonaromatically bound, basic nitrogen atoms (on a statistical average), of which at least two are primary and/or secondary amino nitrogen atoms.

When a commercial polyisocyanate, e.g. a toluylene diisocyanate-isomeric mixture, is mixed with commercial ethylene diamine or diethylene triamine, the expected vigorous, almost uncontrollable, reaction takes place. However, it has been surprisingly found that when a comparable quantity of triethylene tetramine or tetraethylene pentamine is used as the reactant amine, the thermal reaction is rather mild and can be easily controlled.

Polyisocyanates can be reacted with the above-described polyamines in accordance with the present invention in a manner which does not require use of problem-creating diluents or expensive apparatus to control the rest of the reaction. Commercially available and pure polyisocyanates (particularly those which are liquid at room temperature) and mixtures thereof can be easily reacted in situ by the process of the invention to produce suspensions of polyureas in the product polyisocyanates. These polyurea suspensions increase the viscosity and flow characteristics of the product isocyanate or polyisocyanate. Such an increase in viscosity and flow characteristics is particularly desirable when these polyisocyanates are to be processed into cellular or noncellular, flexible or rigid plastics. The products of the process according to the present invention, when used as structural components in the preparation of polyurethane plastics permit modification of the final products, thereby increasing the possible variations of commercial polyurethanes.

DETAILED DESCRIPTION OF THE INVENTION

The present invention is a process for preparing modified polyisocyanates in which an organic polyisocyanate is reacted with a polyamine present in less than a stoichiometric amount. Polyamines suitable to the practice of this invention are polyamines or polyamine mixtures having more than three nonaromatically bound, basic nitrogen atoms of which at least two are primary and/or secondary amino nitrogen atoms.

In principle, any organic polyisocyanates are suitable starting materials for the process of the invention. Suitable polyisocyanates are described, for example, in U.S. Pat. No. 4,058,492, column 3, line 33 to column 4, line 61 (herein incorporated by reference) and in the literature references cited therein. Diisocyanates of the formula $$R(NCO)_2$$

are among the preferred polyisocyanates. R in the above-given formula may represent a difunctional, saturated aliphatic hydrocarbon radical having from 6 to 10 carbon atoms, a difunctional, saturated cycloaliphatic hydrocarbon radical having from 4 to 15 carbon atoms, a difunctional aromatic hydrocarbon radical having from 6 to 17 carbon atoms or a xylylene radical.

Typical examples of the preferred diisocyanates are hexamethylene diisocyanate; dodecamethylene diisocyanate; cyclobutane diisocyanate; 1-methyl-2,4-diisocyanato-cyclohexane; 1-isocyanato-3,3,5-trimethyl-5-methyl-5-isocyanatomethyl-cyclohexane (IPDI); 4,4'-diisocyanato-dicyclohexylmethane; 2,4-diisocyanato-toluene, the commercial mixtures thereof containing 2,6-diisocyanato-toluene; 4,4'-diisocyanato-diphenylmethane, the commercial mixtures thereof containing 2,2'- and 2,4'-diisocyanato-diphenylmethane and p-xylylene diisocyanate. Mixtures of these polyisocyanates may also be used. Diisocyanates which are liquid are particularly preferred.

2,4-diisocyanato-toluene or commercial mixtures thereof containing up to 35% by weight (based on the total mixture) of 2,6-diisocyanato-toluene are among the most preferred reactant polyisocyanates of the invention. Mixtures of difunctional isocyanates containing up to 50% by weight (based on the total polyisocyanate mixture) of polyfunctional polyisocyanates are also particularly preferred. Polyfunctional polyisocyanates produced by phosgenating aniline/formaldehyde condensates in accordance with methods known to those in the art are also among the most preferred starting materials.

The polyamine starting materials which may be used in the present invention are either (a) polyamines which contain more than three nonaromatically bound, basic nitrogen atoms, of which at least two are primary and/or secondary amino nitrogen atoms, or (b) polyamine mixtures which contain more than three nonaromatically bound, basic nitrogen atoms (on the statistical average) of which at least two are primary and/or secondary amino nitrogen atoms.

The polyamines or polyamine mixtures preferably have an average molecular weight between 146 and 300. Polyalkylene polyamines or commercial polyalkylene polyamine mixtures having more than three nonaromatically bound, basic nitrogen atoms of which at least two are primary and/or secondary amino nitrogen atoms are particularly preferred starting materials. Triethylenetetramine, tetraethylenepentamine, tripropylenetetramine and tetrapropylenepentamine are examples of suitable polyalkylene polyamines. Commercial mixtures of the polyalkylene polyamines are included in the above-mentioned polyalkylene polyamine mixtures. These polyalkylene polyamines may also contain small quantities of other polyamines such as N-(2-aminoethyl)-piperazine; N,N'-bis-(2-aminoethyl)-piperazine, N-(2-aminopropyl)-piperazine or N,N'-bis(2-aminopropyl)-piperazine and/or branched-chain isomers of the above-mentioned polyamines. Commercial triethylene tetramine and commercial tetraethylene pentamine are the particularly preferred polyamine starting materials.

The polyisocyanate starting material is introduced at a temperature of between 5° and 150° C., preferably at a temperature of from 15° to 75° C., and most preferably at room temperature. The amine component is then added with thorough stirring. Because only a slight heat effect is observed, the process may be carried out very quickly. The amine component is added in quantities of from 0.1 to 50% by weight, preferably from 0.5 to 10% by weight (based on the total mixture). Care must be taken, however, that the equivalent ratio between isocyanate groups of the reactant polyisocyanate and the primary or secondary amino groups of the reactant amine is greater than 2:1. After mixing the starting components vigorously for a short time, the reaction product containing isocyanate and urea groups is suspended in the excess reactant polyisocyanate.

The process of the present invention may also be carried out using compounds in addition to the above-described polyamines, which additional compounds contain hydrogen atoms that are reactive towards isocyanate groups. Examples of these additional compounds include aliphatic polyols (which may contain ether groups) having a molecular weight of 62 to 7,000 and single polyamines such as ethylene diamine or propylene diamine. If such additional compounds are used, care must be taken to ensure that the equivalent ratio of all of the isocyanate groups of the polyisocyanate starting material to all groups which are reactive toward the isocyanate groups is greater than 2:1.

Small quantities of single polyamines of the type mentioned above may be used as long as the average of at least three nonaromatically bound basic nitrogen atoms having two or more primary and/or secondary amino nitrogen atoms is preserved. If this average is not maintained due to use of excess amounts of single polyamines of the type mentioned above, the disadvantageous phenomena described above are encountered. The use of additional compounds which react with the reactant polyisocyanate is not preferred, however.

The reaction according to the process of the present invention may also be carried out in the presence of inorganic or organic fillers. Inert additives which are conventionally used in polyurethane chemistry may also be used alone or in combination with such fillers. These auxiliary agents and additives may be incorporated in the products of the process of the invention even after their preparation.

The products of the process of the present invention may also be used in reactions known to those in the art for the modification of organic polyisocyanates. The known carbodiimization, allophanatization and prepolymerization reactions are illustrative of such modification reactions.

The products of the process according to the invention are suspensions of reaction products formed from the reactant polyisocyanate and amine, which suspensions contain isocyanate and urea groups in the excess polyisocyanate starting material. These suspensions generally have increased viscosity and occasionally increased thixotropic properties with respect to the pure isocyanate starting material.

The products of the process of the present invention may be mixed with conventional polyisocyanates. These polyisocyanates are particularly useful starting materials for the preparation of polyurethane plastics by the known isocyanate-polyaddition process. For this purpose, the polyisocyanate of the present invention may be used either alone or in admixture with other polyisocyanates as a polyisocyanate component in combination with the coreactants conventional in polyurethane chemistry, in conventional ratios (by quantity).

Having thus described our invention, the following examples are given by way of illustration. All figures expressed in "parts" relate to parts by weight unless otherwise indicated.

EXAMPLES

COMPARATIVE EXAMPLE A 1425 parts of a commercial mixture of 80% by weight of 2,4-toluylene diisocyanate and 20 parts by weight of 2,6-toluylene diisocyanate were introduced into a two-liter polyethylene flask and stirred with a high-speed stirrer. 75 parts of ethylene diamine were then poured into this mixture. A vigorous reaction commenced immediately. The temperature increased from room temperature to 96° C.

COMPARATIVE EXAMPLE B

The process was carried out in accordance with the procedure described in Comparative Example A with the exception that commercial diethylene triamine was used as the amine. A vigorous reaction commenced immediately and the temperature rose above 70° C. Simultaneously, swelling and the formation of lumps was observed.

Both of these Comparative Examples show that the expected vigorous reaction between aliphatic amines and aromatic isocyanates does occur.

EXAMPLE 1

1425 parts of the polyisocyanate used in Comparative Example A were reacted with 75 parts of commercial triethylene tetramine in accordance with the procedure described in Comparative Example A. In addition to containing 70.4% by weight of linear polyamine (determined by gas chromatography), triethylenetetramine also contained 14.4% by weight of branched isomers, 9.0% by weight of cyclization products (particularly N,N'-bis-(2-amino ethyl)-piperazine) and 6.2% by weight of other by-products. This corresponds to an NCO/NH equivalent ratio of approximately 9:1. No immediate vigorous reaction took place, but after approximately five minutes, the temperature gradually rose to about 35° C. and a fine particled, slightly thixotropic suspension of the colorless reaction product in the polyisocyanate formed. Stirring was stopped after approximately ten minutes. After sixty minutes, the reaction mixture, which had cooled in the meantime, was again shaken vigorously. The resulting suspension had a viscosity of approximately 8000 mPas (measured at 20° C.).

Where double or half the quantity of amine used in the above-described procedure was used, the course of the reaction was virtually the same. A thixotropic polyurea suspension in the polyisocyanate was obtained in each case.

EXAMPLE 2

The process was carried out as described in Example 1 using the same quantities of the starting materials, with the exception that commercial tetraethylene pentamine which contained 45.9% by weight of linear polyamines, 16.2% by weight of branched polyamines, 32.2% by weight of cyclic polyamines, and a residual fraction of 5.7% by weight of other amines was used as the amine component. In this case, the reaction temperatures rose from approximately 18° C. to approximately 25° C.

It can be seen from Examples 1 and 2 that an unexpectedly mild reaction occurs between reactive aromatic polyisocyanates and polyethylene polyamines containing more than three basic nitrogen atoms. The mildness of the reaction permits preparation of suspensions of reaction products of polyalkylene polyamines containing more than three basic nitrogen atoms by a simple in situ reaction in the presence of a polyisocyanate. The isocyanates are thereby modified without difficulty.

EXAMPLE 3

The process was carried out as in Example 1 using the same quantities of the starting materials, with the exception that commercial isophorone diisocyanate (IPDI) was used instead of the toluylene diisocyanate used in Example 1. With slight heating, a fine particled suspension of the reaction product of isophorone diisocyanate and triethylene tetramine was obtained. This suspension had a viscosity of approximately 4000 mPas/20° C.

EXAMPLE 4

A liquid polyisocyanate mixture of the diphenylmethane series was prepared by phosgenating aniline/formaldehyde condensates in a manner known per se. This polyisocyanate mixture had an isocyanate group content of 31% by weight and a viscosity of 650 mPas at 20° C. 100 parts of this polyisocyanate mixture were stirred intensively with 20 parts by weight of the commercial triethylene tetramine from Example 1 at room temperature. There was no significant temperature increase during this reaction. However, a pulpy mixture was obtained which solidified during the course of a few hours.

When the experiment was repeated using only 10 parts by weight of commercial triethylene tetramine, a polyisocyanate mixture was obtained which thickened to approximately 5000 mPas/20° C. This product was as suitable for the further processing into polyurethane plastics as the products described in Examples 1 through 3.

EXAMPLE 5

9850 parts of a commercial mixture of 65% by weight of 2,4-toluylene diisocyanate and 35% by weight of 2,6-toluylene diisocyanate were mixed in a stirring vessel at 35° C. with 150 parts of the technical triethylene tetramine used in Example 1. This mixture was stirred intensively for fifteen minutes.

After 24 hours, the viscosity of the resulting suspension was measured as 960 mPas at 22° C. The isocyanate starting material had a viscosity of 10 mPas.

EXAMPLE 6

4925 parts of the isocyanate used in Example 5 were mixed with 4925 parts of a polyisocyanate mixture obtained by phosgenating an aniline/formaldehyde condensate of the diphenylmethane series, said phosgenated mixture having a viscosity of 200 mPas/20° C. 150 parts of triethylene tetramine were added to this isocyanate mixture with intensive stirring at 40° C. The mixture was stirred for approximately fifteen minutes. The temperature was then increased to 65° C. by using a water bath. The mixture was then cooled. After 24 hours, a viscosity of 1900 mPas at 22° C. was measured. (The starting mixture had had a viscosity of approximately 25 mPas.)

EXAMPLE 7

In a process similar to that of Example 1, 1500 parts of a mixture of 80% by weight of the isocyanate used in Comparative Example A and 20% by weight of the commercial polynuclear isocyanate mixture used in Example 6 were reacted with 30 parts of triethylene tetramine with intensive stirring at room temperature. The starting isocyanate mixture had a viscosity of approximately 10 mPas, while the product suspension had a viscosity of 3200 mPas at 20° C. after 50 hours.

The suspensions obtained in Examples 5 to 7 had a slightly thixotropic nature and were suitable as starting materials for the preparation of polyurethane plastics, e.g., polyurethane foamed plastics, according to conventional formulations.

What is claimed is:

1. A process for the preparation of modified polyisocyanates in which organic polyisocyanates are reacted with less than a stoichiometric quantity of polyamine, said polyamine being taken from the class consisting of:
   (a) a polyamine containing more than three nonaromatically bound, basic nitrogen atoms, of which at least two are primary and/or secondary amino nitrogen atoms, and
   (b) a polyamine mixture which contains an average of more than three nonaromatically bound, basic nitrogen atoms, of which at least two are primary and/or secondary amino nitrogen atoms.

2. The process of claim 1, wherein the polyisocyanate is a diisocyanate of the formula R(NCO)

wherein
   R represents a difunctional, saturated aliphatic hydrocarbon radical having from 6 to 10 carbon atoms; a difunctional saturated cycloaliphatic hydrocarbon radical having from 4 to 15 carbon atoms; a difunctional aromatic hydrocarbon radical having from 6 to 17 carbon atoms or a xylylene radical.

3. The process of claim 1, wherein the polyamine is a polyalkylene polyamine containing more than three basic nitrogen atoms on the statistical average.

4. The process of claim 2, wherein the polyamine is a polyalkylene polyamine containing an average of more than three basic nitrogen atoms.

5. The process of claim 1, wherein the polyisocyanate is 2,4-diisocyanato-toluylene or a mixture thereof containing 2,6-diisocyanato-toluene and the polyamine is triethylene tetramine.

* * * * *